United States Patent [19]

Jamshidi

[11] Patent Number: 5,429,138
[45] Date of Patent: Jul. 4, 1995

[54] BIOPSY NEEDLE WITH SAMPLE RETAINING MEANS

[75] Inventor: Khosrow Jamshidi, St. Paul, Minn.

[73] Assignee: KorMed, Inc., Edina, Minn.

[21] Appl. No.: 215,859

[22] Filed: Mar. 22, 1994

Related U.S. Application Data

[63] Continuation-in-part of Ser. No. 71,694, Jun. 3, 1993, abandoned.

[51] Int. Cl.⁶ .............................................. A61B 10/00
[52] U.S. Cl. ...................................................... 128/753
[58] Field of Search .............................. 128/751–754, 128/749; 604/37, 167

[56] References Cited

U.S. PATENT DOCUMENTS

| | | | |
|---|---|---|---|
| 3,330,268 | 7/1967 | Goldsmith | 128/2 |
| 3,470,867 | 10/1969 | Goldsmith | 128/2 |
| 3,598,108 | 8/1971 | Jamshidi | 128/2 |
| 3,628,524 | 12/1971 | Jamshidi | 128/2 |
| 3,630,192 | 12/1971 | Jamshidi | 128/2 |
| 3,766,916 | 10/1973 | Moorehead et al. | 604/167 |
| 3,800,783 | 4/1974 | Jamshidi | 128/2 |
| 3,882,849 | 5/1975 | Jamshidi | 128/2 |
| 3,929,123 | 12/1975 | Jamshidi | 128/2 |
| 3,987,895 | 10/1976 | Jamshidi | 206/72 |
| 4,163,446 | 8/1979 | Jamshidi | 128/754 |
| 4,655,226 | 4/1987 | Lee | 128/754 |
| 4,922,602 | 5/1990 | Mehl | 29/460 |

FOREIGN PATENT DOCUMENTS

1711849A1  2/1992  U.S.S.R. ............................ 128/754

OTHER PUBLICATIONS

"How to Reassemble the Reusable Jamshidi Bone Marrow Biopsy/Aspiration Needle", Baxter Healthcare Corporation, Copyright 1990.

"Jamshidi Bone Marrow Biopsy/Aspiration Needles", Kormed, Inc. Subsidiary of American Hospital Supply Corporation, Copyright Oct., 1980.

"The Jamshidi Needle/Syringe—Completely Disposable", Kormed, Inc.

Primary Examiner—Max Hindenburg
Attorney, Agent, or Firm—Nawrocki, Rooney & Sivertson

[57] ABSTRACT

A biopsy needle assembly and kit for acquiring a sample of tissue and method of using the same. The biopsy needle assembly includes a needle having a lumen extending therethrough terminating at its proximal end with a handle having a bore therethrough connected to said end. The proximal end of the bore of the handle includes a conical tapered section which increases in diameter from a point distal of the proximal end of the handle to the proximal end of the handle for sealably receiving an aspirator bulb. The aspirator bulb is utilized to aid in acquiring a tissue sample and retaining it within the lumen of the needle during removal of the biopsy needle assembly. An elastomeric plug can also be utilized to assist in retaining a sample. The biopsy needle assembly also includes a stylet sized for disposition within the lumen of the needle and extending beyond the distal end of the needle to provide a cutting edge which is formed thereon. The device also includes means for preventing rotation of the stylet relative to the needle and means for releasably securing the stylet in a fully inserted position.

5 Claims, 3 Drawing Sheets

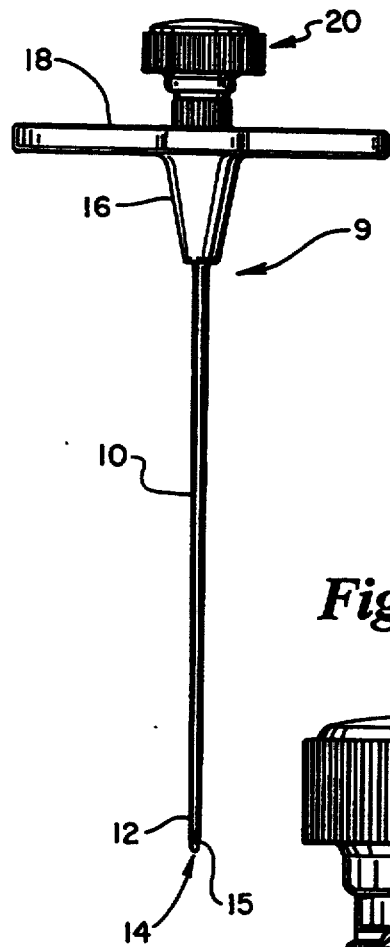
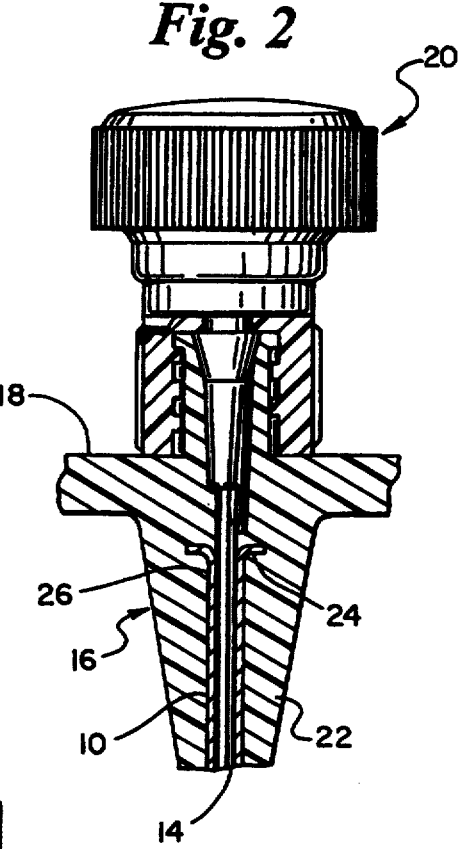
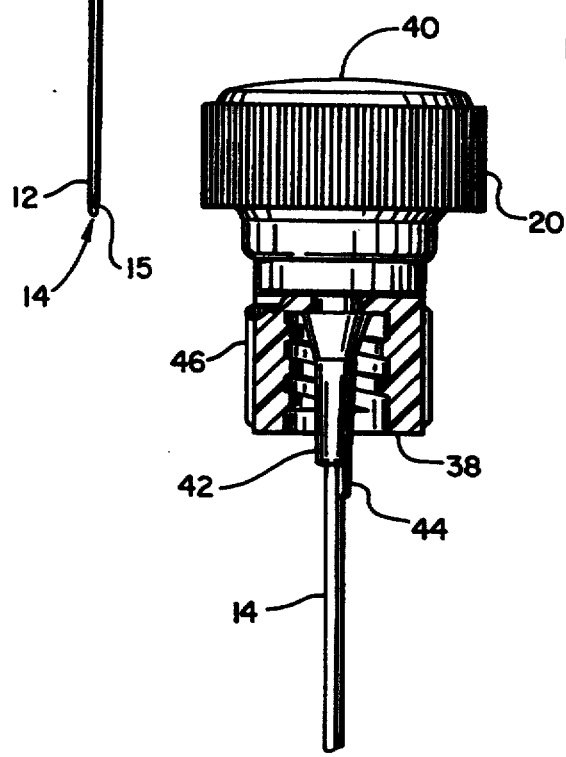
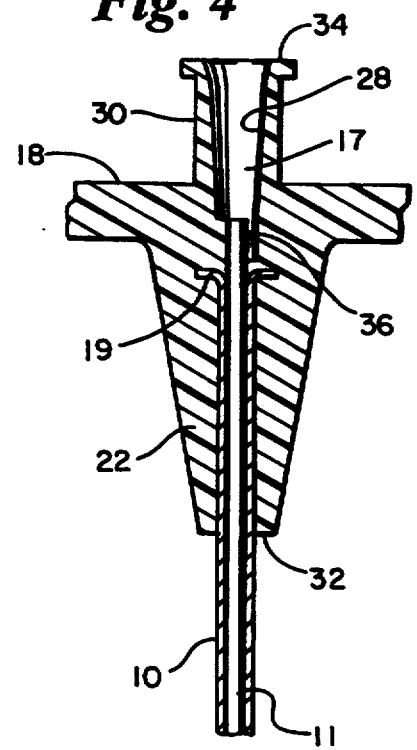

BIOPSY NEEDLE WITH SAMPLE RETAINING MEANS

RELATED APPLICATIONS

This application is a continuation-in-part of U.S. patent application Ser. No. 08/071,694, filed Jun. 3, 1993, now abandoned.

TECHNICAL FIELD

The present invention deals broadly with the field of medical devices. More narrowly, however, it is directed to a device and a method for acquiring an internal sample of tissue from a patient. The device is generally referred to as a biopsy needle. The device of the present invention is particularly useful for acquiring a sample of bone marrow, but may be utilized to sample tissue from muscles or organs.

BACKGROUND OF THE INVENTION

Devices for acquiring internal tissue samples from a patient are generally known. For example, Jamshidi (U.S. Pat. No. 3,628,524) discloses a biopsy needle assembly which includes a needle and stylet. The disclosed biopsy needle may be utilized for sampling softer tissues such as liver, kidney, skin, and muscle tissue. The biopsy needle can also include a rasp-like exterior surface, a cutting edge, to be employed in biopsy needles used in obtaining bone and bone marrow biopsy specimens.

The needle disclosed by Jamshidi in U.S. Pat. No. 3,628,524 includes an elongate, substantially cylindrical body having a lumen therethrough. The device further includes a styler which is similar in shape and length to the needle, which is adapted to be inserted into the needle in snug-fitting relation.

When assembled for use, the stylet is inserted into the needle and a locking pin is included to hold the stylet in place. When fully inserted the distal end of the stylet and needle are arranged in a predetermined relation to present a closed end surface which is utilized for penetrating tissue or bone.

Jamshidi further discloses that the stylet, as inserted into the needle and interlocked, exposes a tapered distal end. The tapered distal end is positioned in a predetermined relation with respect to the distal cutting edge on the needle whereby a closed symmetrical end surface is disposed substantially in a single plane. The needle is then inserted into the patient to a desired depth. Inserting the device can require penetration of bone which will necessitate rotating the needle and stylet assembly about its longitudinal axis to produce a boring effect caused by the rasp-like surfaces on the distal end of the needle.

When the distal end of the needle has reached the tissue from which the specimen is to be removed, the stylet is then removed from the needle and the needle may then again be revolved about its longitudinal axis while urging it forwardly. The moving of the needle produces a cutting action of the tissue and allows the specimen to be collected interiorly of the needle. After the specimen is collected, the needle is then removed from the patient.

Jamshidi (U.S. Pat. No. 3,598,108) discloses a similar biopsy device as that disclosed above. However, it is further disclosed that the stylet is first removed and the biopsy specimen is collected in a separate sleeve member which is inserted within the needle. The needle remains in place after the sample is taken so that a heat transfer means such as a microcauter or a cryoprobe may be introduced into the needle. These devices are utilized to reduce or prevent bleeding.

In U.S. Pat. No. 4,163,446, Jamshidi discloses a pad for use in combination with a bone marrow biopsy needle which is adapted to be slipped over the proximal end of the needle to provide an enlarged surface for distributing the pressure across the palm of the hand of the user. The device includes a generally disc-shaped palm engaging surface along a needle enveloping sleeve for releasable attachment to the biopsy needle.

Finally, Jamshidi (U.S. Pat. No. 3,630,192) discloses a biopsy needle having a sheath which is particularly adapted for use in the obtaining of biopsy samples from certain floating organs. The sheath disclosed by Jamshidi prevents accidental damage to such organs which would result in undesirable bleeding or other complications.

In utilizing all of these prior art devices, once a tissue sample is acquired within the lumen of the biopsy needle, the needle must be withdrawn with the sample included. However, there is nothing disclosed that will assure that the sample is held within the lumen of the needle during extraction. Thus, a problem arises, in use, when a portion of the tissue sample or fluid collected within the needle is allowed to drain into the track made by the incision. The problem is two-fold, in that the sample loss reduces the size of the specimen to be analyzed, and second, it is undesirable to deposit the tissue sample away from its source within the patient.

Accordingly, the need exists for a device for acquiring a tissue sample or a biopsy needle and method of use which prevents the loss of tissue sample or fluid sample during extraction of the needle. The device and method should include an apparatus which prevents accidental loss of any portion of the sample during removal of the biopsy needle assembly. Further, these features should be of simple design to prevent dramatically increasing the cost of the overall biopsy needle assembly and procedure.

The present invention addresses these needs as well as other problems associated with existing biopsy needles or devices for acquiring internal tissue samples. The present invention also offers further advantages over the prior art and solves problems associated therewith.

SUMMARY OF THE INVENTION

The present invention is a device for acquiring a sample of tissue or fluid from a patient, generally referred to herein as a biopsy needle assembly. The invention may also be packaged as a kit which includes all necessary components for performing sampling of tissue. The invention also includes a method for utilizing the device of the present invention in acquiring the biopsy, fluid or tissue sample. The biopsy needle assembly is specifically designed to include features which prevent the loss of any portion of the tissue or fluid sample during extraction of the biopsy needle from the incision track after a sample has been captured within the lumen of the needle. Thus, the biopsy needle assembly includes a tapered section defining a generally conical surface at its proximal end in fluid communication with the needle lumen. An aspirator bulb may be sealably inserted into the tapered section to provide suction which aids in both acquiring and retaining the tissue and/or fluid sample.

The biopsy needle assembly of the present invention can also include a tapered elastomeric or polymeric plug which is adapted to be received into the tapered section at the proximal end of the needle assembly. With this embodiment, a sample may be drawn into the needle lumen assisted by the aspirator bulb. Then the aspirator bulb can be removed and replaced with the tapered plug which will hold the sample in place as the needle is withdrawn from the tissue.

In another preferred embodiment, means for preventing plugging of the needle lumen at its proximal end or through the lumen into the aspirator bulb is provided. This means for preventing plugging of the needle can include a transition region proximate the distal end of the aspirator bulb. The transition region is split into at least two lumens whose radial center is not coincidental with the radial center of the needle lumen. Plugging of the lumen into the aspirator bulb by tissue is reduced by diverting the flow and terminating the needle lumen at its proximal end with a surface directly in the flow path which can stop the movement of tissue into the aspirator bulb region.

The biopsy needle assembly of the present invention includes a needle having a distal end, a proximal end, and a lumen which extends from the distal end to the proximal end. The needle is generally cylindrical in shape and preferably made of metal.

A handle having a distal end, a proximal end, and a bore extending from the distal end to the proximal end is also included. The proximal end of the lumen of the needle is secured in fluid communication with the distal end of the bore of the handle. The proximal end of the bore of the handle includes a tapered section. The tapered section defines a generally conical surface of increasing diameter from a point distal of the proximal end of the handle to the proximal end of the handle. This conical surface is utilized to sealably receive an aspirator bulb or plug as disclosed hereinafter.

The biopsy needle assembly also includes a stylet having a distal end and a proximal end. The stylet is generally a cylindrical elongated shaft which is solid or can be hollow with at least the distal end closed or capped. The distal end of the stylet includes a cutting edge formed thereon which can be a beveled, machined surface. The stylet is sized for removable disposition through the bore of the handle and the lumen of the needle. In a fully inserted position, the distal end of the stylet extends beyond the distal end of the needle so that the cutting edge is exposed.

Means for preventing rotation of the stylet relative to the needle when the stylet is in a fully inserted position are also included. Further, means for releasably securing the stylet in a fully inserted position are included.

The handle of the biopsy needle of the present invention can also include a cross-member disposed generally perpendicular to the bore of the handle. This cross-member can be located intermediate the distal and proximal ends of the handle to provide structure for gripping the assembly and rotating it for insertion into the patient.

The stylet may also include a knob having a distal end and a proximal end fixedly attached at its distal end to the proximal end of the stylet. The means for preventing rotation of the stylet relative to the needle may be incorporated into this knob. Thus, a registration projection can extend distally from the knob proximate the stylet surface. A registration slot may be positioned in the bore of the handle to receive the registration projection when the stylet is in a fully inserted position. In this way, rotation of the stylet relative to the needle during insertion into the patient is prevented.

The means for releasably securing the stylet in the fully inserted position may include any known means. This could include a threaded connection, or can include the combination of a male luer fitting and female luer fitting. For example, the male luer fitting may be located in a concentric position with the bore of the handle and extend distally from the proximal end of the handle. A female luer fitting concentric with the stylet extending distally from a point intermediate the knob can also be included which cooperates with the male luer fitting to releasably secure the stylet in a fully inserted position.

A kit for acquiring a sample of tissue embodied in the present invention would include an aspirator bulb. The aspirator bulb has a distal end with a conical taper of decreasing diameter approximating the conical surface of the bore of the handle. In use, the aspirator bulb would be sealably positioned within the conical portion of the bore to provide suction during sampling of tissue or fluid and assist in retaining the sample within the lumen of the needle during withdrawal of the needle. Alternatively or additionally, a kit for acquiring a sample of tissue in the present invention can include a conically tapered elastomeric plug approximating the conical surface of the bore of the handle. Upon extracting a sample into the needle, this plug can be inserted into the bore of the handle to assist in retaining the sample.

The method for acquiring an internal tissue sample utilizing the above device, assembly or kit would include providing a biopsy needle assembly as disclosed above. The stylet is then positioned in the fully inserted position within the lumen of the needle. The biopsy needle assembly is then inserted, with the stylet in the fully inserted position, at the desired location within the patient. The cutting edge is utilized to assist in reaching a desired depth of insertion. The stylet is then removed.

The aspirator bulb, which has an internal volume, is depressed to a depressed position to expel a portion of the internal volume. The aspirator bulb is then sealably positioned within the conical portion of the bore of the handle. The pressure applied to depress the bulb is then released to provide suction which draws tissue and fluid into the lumen of the needle. The device, with the aspirator bulb remaining sealably positioned, is withdrawn, thus retaining the sample within the lumen of the needle. Alternatively, the aspirator bulb may be removed prior to withdrawing the device and the elastomeric plug substituted therefore to retain the sample when the needle is withdrawn.

These and various other advantages and features of novelty which characterize the present invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter in which there are illustrated and described preferred embodiments-of the present invention.

BRIEF DESCRIPTION OF THE DRAWINGS

In the drawings, in which like reference numerals indicate corresponding parts or elements of preferred embodiments of the present invention throughout the several views:

FIG. 1 is a side elevational view of a biopsy needle assembly of the present invention with a stylet fully inserted;

FIG. 2 is an enlarged fragmentary detail view of the proximal portion of the biopsy needle assembly with the stylet fully inserted;

FIG. 3 is an enlarged fragmentary detail of the proximal portion of the stylet having a knob assembly thereon;

FIG. 4 is a fragmentary detail view of the needle and handle of the present invention with stylet removed;

DETAILED DESCRIPTION OF THE INVENTION

Figure 5:
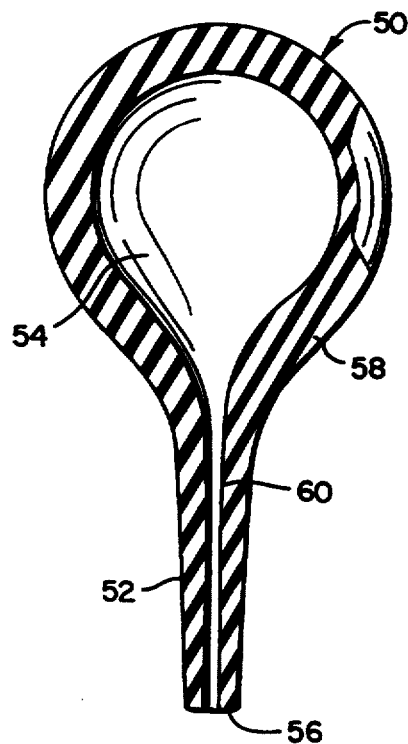
FIG. 5 is a side elevational view of an aspirator bulb.

Detailed embodiments of the present invention are disclosed herein. It is to be understood, however, that the disclosed embodiments are merely exemplary of the present invention which may be embodied in various forms. Therefore, specific details disclosed herein are not to be interpreted as limiting, but rather as a basis for the claims and as a representative basis for teaching one of skill in the art to variously practice the invention.

Referring now to FIG. 1, a side elevational view of a biopsy needle assembly 9 with a stylet 14 fully inserted therein is depicted. Referring also to FIGS. 2–4, the biopsy needle assembly 9 of FIG. 1 is depicted in enlarged fragmentary detail in each illustration to detail specific features of the present invention. FIG. 2 provides a detailed fragmentary view of the proximal portion of the biopsy needle assembly 9 with the stylet 14 fully inserted. FIG. 3 depicts the stylet 14 separated from the needle 10 while FIG. 4 depicts the needle 10 with the stylet 14 removed.

The biopsy needle assembly 9 of the present invention includes a needle 10 which has a distal end 12, a proximal end 26 and a lumen 11 extending from the distal end 12 to the proximal end 26. The needle 10 is generally an elongated cylindrical member having a generally cylindrical lumen therethrough. The needle 10 is preferably constructed from metal. The distal end 12 of the needle 10 is preferably tapered relative to the needle's longitudinal axis to cooperate with a cutting edge of the stylet 14 when in use as described below.

A handle 16 having a distal end 32, a proximal end 34 and a bore 17, extending from the distal end 32 to the proximal end 34, is included. The proximal end 26 of the lumen 11 of the needle 10 is secured in fluid communication with the distal end 32 of the bore 17 of the handle 16. The means used to secure the needle to the handle can be any known means. This could include utilizing an adhesive or threaded connection. As depicted in FIG. 4, it can also include molding the handle 16 around a flared proximal end 19 of the needle 10 to prevent separation of handle 16 and needle 10. Any known molding technique, such as injection molding, could be utilized.

The proximal end 34 of the bore 17 of the handle 16 includes a tapered section 28. The tapered section defines a generally conical surface of increasing diameter from a point remote from the proximal end 34 of the handle 16 to the proximal end 34 of the handle 16. This conical surface is specifically designed for sealably receiving an aspirator bulb 50 as depicted in FIG. 5. A stylet 14 having a distal end 15 and a proximal end 42 is also included in the biopsy needle assembly 9 of the present invention. The distal end 15 includes a cutting edge formed thereon. The cutting edge can be formed by machining the distal end 15 to taper the end relative to the longitudinal axis of the stylet 14 to create a distally extending cutting edge. The stylet 14 is sized for removable disposition through the bore 17 of the handle 16 and the lumen 11 of the needle 10. When the stylet 14 is in a fully inserted position as depicted in FIG. 1, the distal end 15 of the stylet 14 extends beyond the distal end 12 of the needle 10 so that the cutting edge is exposed. As previously discussed, the cutting edge and distal end of the needle are shaped to provide a continuous, closed surface. This provides a proper cutting surface and improves the ease with which the biopsy needle assembly 9 may be inserted into the patient.

As the biopsy needle assembly 9 is inserted into a patient, the device can be rotated to facilitate the cutting action, especially when cutting through bone. Means can be provided for preventing rotation of the stylet 14 relative to the needle 10 during such cutting operations. Further, means can also be provided for securing the stylet 14 in a fully inserted position. For ease in operation, the handle 16 can also include a cross-member 18 which is disposed generally perpendicular to the bore 17 of the handle 16 at a location intermediate the distal end 32 and proximal end 34 of the handle 16. The cross-member 18 assists in directing the biopsy needle assembly 9 and provides a means for gripping and rotating the device during use.

The biopsy needle assembly 9 can also include a knob 20 which also has a proximal end 40 and distal end 38. The knob 20 can be fixedly attached at its distal end 38 to the proximal end 42 of the stylet 14. The means for releasably securing the stylet in a fully inserted position and the means for preventing rotation of the stylet relative to the needle in a fully inserted position can be incorporated into the knob 20.

In a preferred embodiment, the means for preventing rotation of the stylet 14 relative to the needle 10 when the stylet 14 is in a fully inserted position can include a registration projection 44. The registration projection 44 extends distally from the distal end 38 of the knob 20 proximate the cylindrical surface of the stylet 14. A registration slot 36 can be positioned in the bore 17 of the handle 16 to receive registration projection 44 when the stylet 14 is in the fully inserted position. In this way, the registration projection 44 and slot 36 cooperate to prevent rotation of the stylet 14 relative to the needle 10.

As previously stated, the means for securing the stylet to the needle in a fully-inserted position can include any known means such as a threaded connection or a cap. In a preferred embodiment, the means for securing the stylet 14 in a fully inserted position can include a male luer fitting in combination with a female luer fitting which cooperate to secure the stylet.

The male luer fitting 30 can be mounted concentric with the bore 17 of the handle 16 and extend distally from the proximal end 34 of the handle 16. A female luer fitting 46 can be mounted concentric with the stylet 14 and extend distally from a point intermediate the knob 20 where, in use, the luer fittings 30, 46 cooperate to releasably secure the stylet 14 in a fully inserted position.

Figure 9:
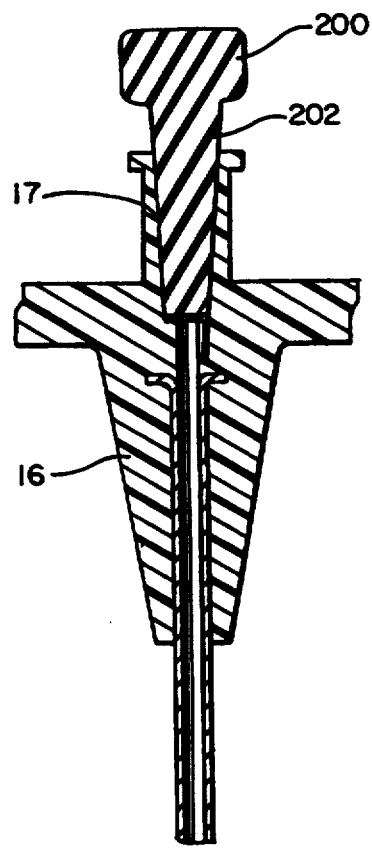

In a preferred embodiment, a biopsy needle assembly 9, as described above, would be incorporated into a kit which would include the necessary components for performing a sampling of desired tissue. The kit would include a biopsy needle assembly as described above. The kit could also include an aspirator bulb 50 as depicted in FIG. 5, an alternative non-plugging aspirator bulb 100 as depicted in FIG. 7, and/or a sample retaining elastomeric plug as depicted in FIG. 9.

Figure 6:
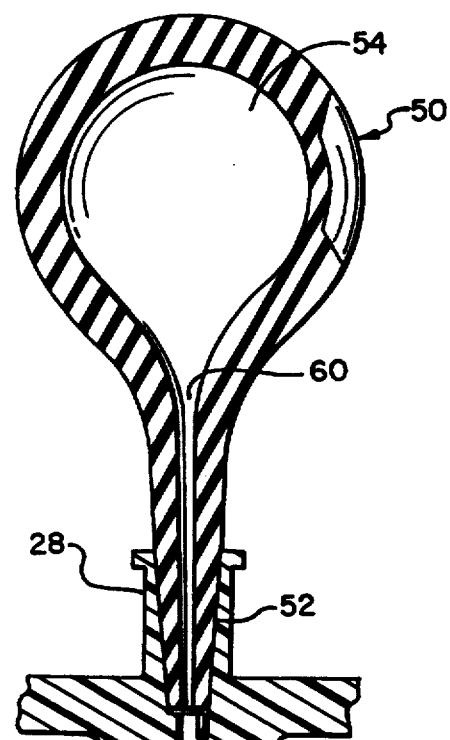
FIG. 6 is a fragmentary side elevational view of an aspirator bulb sealably inserted into the tapered conical section of the handle for retaining a sample in the lumen of the needle.

The aspirator bulb 50 has a distal end 56 which has a conical taper 52 of decreasing diameter proximate the conical surface of the bore 17. In use, the aspirator bulb 50, as depicted in FIG. 6, is sealably positioned in the conical portion of the bore 17 to provide suction during the sampling of tissue and to retain the tissue sample within the lumen 11 of the needle 10. Although the design of the aspirator bulb 50 may vary, in general, it should include an internal volume 54 which may be voided when the aspirator bulb 50 is compressed. The aspirator bulb 50 also includes a duct 60 in fluid communication with the internal volume 54 and the distal end 56 of the aspirator bulb 50.

Figure 7:
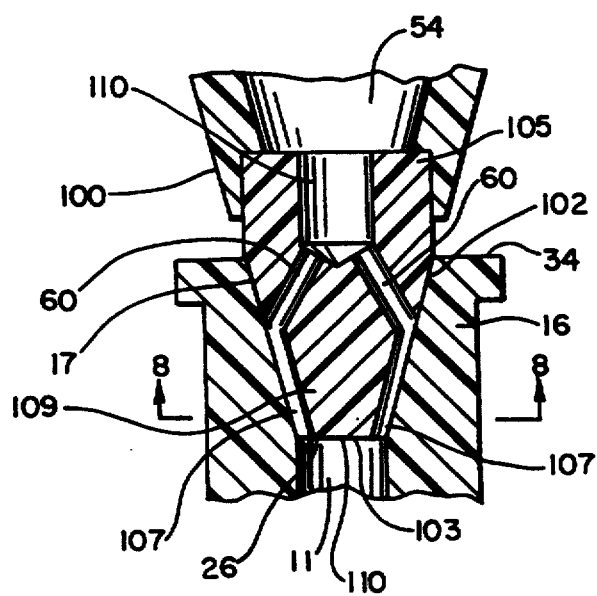
FIG. 7 is a fragmentary detailed view of the transition area of an aspirator bulb in an alternative embodiment.
Figure 8:
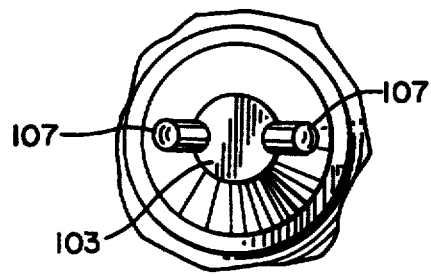
FIG. 8 is a fragmentary cross-sectional view of the transition region of FIG. 7 along line 8—8; and, FIG. 9 is a fragmentary side elevational view of an elastomeric plug sealably inserted into the tapered conical section of the handle for retaining a sample in the lumen of the needle.

Next referring to FIGS. 7 and 8, a preferred design of a non-plugging aspirator bulb 100 is depicted inserted into the proximal end 34 of the handle 16 and sealingly engaging the conical surface of the bore 17. With this embodiment, the aspirator bulb 100 is designed to prevent tissue from entering and plugging the duct 60 which is in fluid communication with the internal volume 54 of the aspirator bulb 100 and the distal end of the aspirator bulb 103. It has been recognized that a duct 60 having a flow path linerally aligned with the lumen 11 of the needle, as depicted in FIG. 6, can cause plugging with tissue when a sample is aspirated utilizing the aspirator bulb 50.

The non-plugging aspirator bulb 100 includes a transition region or section 105 proximate its distal end 103. The transition region 105 provides fluid communication between the proximal end 26 of the needle 10 with the internal volume 54 of the aspirator bulb 100. The transition region 105 preferably includes two ducts 60 which each have a flow path which is not aligned in linear fashion with the lumen 11 of the needle 10 when the distal end 103 of the aspirator bulb 100 is sealingly inserted into the conical taper 17 of the handle 16.

As depicted in FIGS. 7 and 8, the ducts 60 include a first and second channel 107 which runs parallel with the conical taper of the bore 17. At a point intermediate the transition region 105, the channels 107 are angularly offset from parallel to the conical taper of the bore 17 and connect to a central bore 110 which is in fluid communication with the internal volume 54 of the aspirator bulb 100. With this design, the fluid flow path between lumen 11 of the needle 10 and internal volume 54 of aspirator bulb 100 is offset in the transition area 105 and prevents plugging. The surface 110 at the distal end of the transition region 105 is directly in the flow path to assist in retaining pieces of tissue which may plug a duct 60 having a flow path in line with the lumen 11 of the needle 10.

Another alternative embodiment of the biopsy needle assembly 9 of the present invention is depicted in FIG. 9. With this embodiment, an elastomeric plug 200 is included with the kit. The elastomeric plug 200 has a conical distal section 202 which may be sealably received within the conical tapered section 17 of the handle 16. The elastomeric plug may be utilized in a preferred method, wherein upon acquiring a tissue or fluid sample within the lumen 11, the aspirator bulb 54 or 100 may be removed and replaced with the elastomeric plug 200 to assist in retaining the sample within the lumen. In a method wherein an aspirator bulb is not utilized, the elastomeric plug 200 could still be utilized to help retain the sample when the needle is retracted from the tissue.

A method utilizing the above-disclosed biopsy needle assembly or kit would first include providing such assembly. With the stylet 14 in a fully inserted position, the biopsy needle assembly 9 is then inserted into a desired location within a patient while utilizing the cutting edge of the distal edge of the stylet 14 to facilitate reaching a desired depth of insertion. The stylet 14 is then removed. The needle can then be inserted deeper to push tissue into the lumen 11.

Utilizing the aspirator bulb 50 or 100 which has an internal volume 54, the aspirator bulb 50 or 100 is compressed to expel a portion of the internal volume 54. The aspirator bulb 50 or 100 is then sealably positioned within the conical portion 28 of the bore of the handle 17. The aspirator bulb 50 or 100 is then released from a compressed disposition to provide suction which facilitates drawing a sample into the lumen 11 of the needle 10. Once the sample is acquired, the biopsy needle assembly 9 may be withdrawn from the point of incision with the aspirator bulb 50 or 100 remaining sealably positioned to help retain the sample within the lumen 11 of the needle 10.

Alternatively, prior to withdrawing the biopsy needle assembly 9, the aspirator bulb 50 or 100 can be removed and replaced with an elastomeric plug 200. Then, the needle may be withdrawn from the point of incision with the elastomeric plug 200 remaining sealably positioned to help retain the sample within the lumen 11 of the needle 10.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed is:

1. A kit for acquiring a sample of tissue comprising:
   (a) a biopsy needle configuration including,
      (1) a needle having a distal end, a proximal end and a lumen extending from said distal end to said proximal end; and
      (2) a handle having a distal end, a proximal end and a bore extending from said distal end to said proximal end with the proximal end of said lumen of said needle being in fluid communication with the distal end of said bore of said handle, said proximal end of said bore of said handle including a tapered section, said tapered section defining a generally conical surface of increasing diameter from a point distal of said proximal end of said handle to said proximal end of said handle;

(b) a stylet having a distal end and a proximal end, said distal end including a cutting edge formed thereon, said stylet sized for removable disposition through said bore of said handle and said lumen of said needle, wherein in a fully inserted position, the distal end of said stylet extends beyond the distal end of said needle so that said cutting edge is exposed;

(c) said stylet and said needle configuration further including,
  (1) means for preventing rotation of said stylet relative to said needle when said stylet is in said fully inserted position; and
  (2) means for releasably securing said stylet in said fully inserted position; and (d) an aspirator bulb, said aspirator bulb having a distal end with a conical taper of decreasing diameter approximating the conical surface of said bore, and a transition region which provides fluid communication between a distal end of said aspirator bulb and an internal volume thereof, said transition region including at least one low channel which is angularly offset from said lumen of said needle to prevent plugging, wherein, in use, said aspirator bulb is sealably positionable within the conical portion of said bore to provide suction during said sampling of said tissue to retain said sample within said lumen of said needle.

2. The kit of claim 1, further comprising an elastomeric plug having a distal end with a conical taper of decreasing diameter approximating the concial surface of the bore, wherein, in use, said elastomeric plug is sealably positionable within the conical portion of said bore to assist in retaining said sample within said lumen of said needle.

3. The kit of claim 1, further comprising a knob, having a distal end and a proximal end, affixedly attached at its distal end to said proximal end of said stylet.

4. The kit of claim 3, wherein said means for preventing rotation of said stylet relative to said needle when said stylet is in said fully inserted position includes,
  (a) a registration projection extending distally from said distal end of said knob proximate said stylet; and
  (b) a registration slot positioned in said bore of said handle to receive said registration projection when said stylet is in said fully inserted position.

5. The kit of claim 3, wherein said means for securing said stylet in said fully inserted position includes,
  (a) a male luer fitting mounted concentric with said bore of said handle extending distally from the proximal end of said handle; and
  (b) a female luer fitting mounted concentric with said stylet and extending distally from a point intermediate said knob, wherein, in use, said luer fittings cooperate to releasably secure said stylet in said fully inserted position.

* * * * *